United States Patent
Holmes et al.

(10) Patent No.: US 8,236,184 B2
(45) Date of Patent: Aug. 7, 2012

(54) METHOD FOR SEPARATING A COMPOSITE LIQUID INTO AT LEAST TWO COMPONENTS

(75) Inventors: Brian M. Holmes, Lakewood, CO (US); Peter Pihlstedt, Stockholm (SE)

(73) Assignee: Terumo BCT, Inc., Lakewood, CO (US)

( * ) Notice: Subject to any disclaimer, the term of this patent is extended or adjusted under 35 U.S.C. 154(b) by 835 days.

(21) Appl. No.: 11/931,582

(22) Filed: Oct. 31, 2007

(65) Prior Publication Data

US 2008/0283473 A1    Nov. 20, 2008

Related U.S. Application Data

(60) Provisional application No. 60/917,794, filed on May 14, 2007.

(51) Int. Cl.
   *B01D 21/26* (2006.01)
   *B01D 37/00* (2006.01)
   *C02F 1/00* (2006.01)

(52) U.S. Cl. ........ 210/787; 210/143; 210/745; 210/782; 210/790; 494/1

(58) Field of Classification Search .................. 210/787, 210/143, 782, 745; 494/1
   See application file for complete search history.

(56) References Cited

U.S. PATENT DOCUMENTS

| | | | |
|---|---|---|---|
| 3,297,244 A | 1/1967 | Hein | |
| 3,326,458 A | 6/1967 | Meryman et al. | |
| 3,679,128 A | 7/1972 | Unger et al. | |
| 3,708,110 A | 1/1973 | Unger et al. | |
| 3,724,747 A | 4/1973 | Unger et al. | |
| 3,737,096 A | 6/1973 | Jones et al. | |
| 3,858,796 A | 1/1975 | Unger et al. | |
| 3,987,961 A | 10/1976 | Sinn et al. | |
| 4,146,172 A | 3/1979 | Cullis et al. | |
| 4,187,979 A * | 2/1980 | Cullis et al. | 494/1 |
| 4,389,207 A | 6/1983 | Bacehowski et al. | |
| 4,405,079 A | 9/1983 | Schoendorfer | |
| 4,421,503 A | 12/1983 | Latham, Jr. et al. | |
| 4,482,342 A | 11/1984 | Lueptow et al. | |
| 4,720,284 A | 1/1988 | McCarty | |
| 4,850,995 A | 7/1989 | Tie et al. | |
| 4,990,132 A | 2/1991 | Unger et al. | |
| 5,114,396 A | 5/1992 | Unger et al. | |
| 5,427,695 A | 6/1995 | Brown | |
| 5,543,062 A | 8/1996 | Nishimura | |

(Continued)

FOREIGN PATENT DOCUMENTS

EP    0499891    8/1992

(Continued)

OTHER PUBLICATIONS

International Search Report for PCT/US2007/083204, May 8, 2008.

*Primary Examiner* — Krishnan S Menon
*Assistant Examiner* — Dirk Bass
(74) *Attorney, Agent, or Firm* — Edna M. O'Conner

(57) ABSTRACT

A method related to using a squeezing or transfer fluid to transfer fluid or components between bags in a centrifuge wherein the squeezing fluid can be reversed to reduce squeezing and such fluid an also be used to build up a over-pressure for rapid movement.

21 Claims, 4 Drawing Sheets

U.S. PATENT DOCUMENTS

| | | | |
|---|---|---|---|
| 5,632,906 A | 5/1997 | Ishida et al. | |
| 5,637,082 A | 6/1997 | Pages et al. | |
| 5,723,050 A | 3/1998 | Unger et al. | |
| 5,738,644 A | 4/1998 | Holmes et al. | |
| 5,874,208 A | 2/1999 | Unger | |
| 5,904,355 A | 5/1999 | Powers et al. | |
| 5,964,724 A | 10/1999 | Rivera et al. | |
| 6,039,711 A | 3/2000 | Headley et al. | |
| 6,261,217 B1 | 7/2001 | Unger et al. | |
| 6,284,142 B1 * | 9/2001 | Muller | 210/745 |
| 6,296,602 B1 | 10/2001 | Headley | |
| 6,315,706 B1 | 11/2001 | Unger et al. | |
| 6,348,031 B1 | 2/2002 | Unger et al. | |
| 6,439,577 B2 | 8/2002 | Jorgensen et al. | |
| 6,656,105 B2 | 12/2003 | Hogberg et al. | |
| 2002/0119880 A1 | 8/2002 | Hogberg et al. | |
| 2004/0026341 A1 | 2/2004 | Hogberg et al. | |
| 2005/0045567 A1 * | 3/2005 | Holmes et al. | 210/782 |
| 2006/0205581 A1 | 9/2006 | Chammas | |

FOREIGN PATENT DOCUMENTS

| | | |
|---|---|---|
| EP | 0771569 | 5/1997 |
| EP | 1566191 | 8/2005 |
| EP | 1 627 651 | 2/2006 |
| WO | WO 92/00145 | 1/1992 |
| WO | WO 01/02037 | 1/2001 |
| WO | WO 01/97943 | 12/2001 |
| WO | WO 03/089027 | 10/2003 |
| WO | WO 2004/018021 | 3/2004 |
| WO | WO2006/071496 | 7/2006 |

\* cited by examiner

METHOD FOR SEPARATING A COMPOSITE LIQUID INTO AT LEAST TWO COMPONENTS

CROSS REFERENCE TO RELATED APPLICATIONS

This application claims the benefit of U.S. Provisional Application No. 60/917,794 filed May 14, 2007.

FIELD OF THE INVENTION

The present invention concerns an apparatus and a method for separating a volume of composite liquid or blood product into at least two components.

BACKGROUND

The apparatus and method of the invention are particularly appropriate for the separation of biological fluids comprising an aqueous component and one or more cellular components. For example, potential uses of the invention include extracting, from a volume of whole blood, a plasma component, a first cellular component including platelets, a second cellular component including mononuclear cells, and a third cellular component including red blood cells and granulocytes.

European patent application EP 1 566 191 describes a method and an apparatus for separating a volume of whole blood into at least two components in accordance with various separation protocols. For example, one protocol provides for the separation of a volume of whole blood into a plasma component, a platelet component, and a red blood cell component. The apparatus comprises a centrifuge adapted to cooperate with various bag sets, in particular a bag set comprising an annular separation bag for whole blood, which is connected to a platelet component bag, a plasma component bag, and a red blood cell component bag. The centrifuge includes:

A rotor for spinning the separation bag and centrifuging the whole blood contained therein, the rotor having a turntable for supporting the separation bag and a central compartment for containing the component bags connected to the separation bag; and A squeezing system for squeezing the separation bag and causing the transfer of the plasma component from the separation bag into the plasma component bag, of the red blood cell component into the red blood cell component bag and, as the case may be, of the platelet component into the platelet component bag.

SUMMARY OF THE INVENTION

One object of the invention is to provide a method of separating a composite liquid into at least a first component and a second component, comprising centrifuging a separation bag containing a volume of composite liquid so as to cause the sedimentation of at least a first component and a second component; squeezing the separation bag to transfer some of the second component to a first transfer line attached to a first transfer bag and the separation bag; stopping the transfer of the second component to the first transfer line; squeezing the separation bag after the stopping step to build up an over-pressure in the separation bag; and transferring, using the over-pressure, a part of the second component remaining in the separation vessel to the transfer bag through the first transfer line wherein the over-pressure causes the second component to rapidly move toward the first transfer bag.

Another object of the invention is to provide a method of adjusting the plasma concentration of platelet product comprising centrifuging a separation vessel containing a volume of a composite liquid into at least a plasma component and a platelet component; squeezing with hydraulic fluid the separation vessel to transfer some of the plasma component to a plasma transfer bag; squeezing with hydraulic fluid the separation vessel to transfer some of the platelet component to a platelet transfer bag; reversing at least one of the squeezing steps by releasing a volume of hydraulic fluid from squeezing the separation vessel; returning a volume of the plasma component related to the volume of released hydraulic fluid to the separation vessel; remixing the returned volume of plasma with residual platelets in the separation vessel; and squeezing the separation vessel to transfer mixed platelets and plasma to the platelet transfer bag.

A further object of the invention is to provide a method of collecting plasma, plasma rich platelets, monocytes and red blood cells from a composite blood product comprising centrifuging a separation bag containing a volume of composite blood product so as to cause sedimentation of plasma, platelets, mononuclear and red blood cells; squeezing the separation bag to transfer some of the plasma to a plasma transfer bag; squeezing the separation bag to transfer some of the platelets to a platelet transfer bag; reversing the squeezing of the separation bag to release pressure on the bag; returning some of the plasma from the plasma transfer bag to the separation bag; remixing some of the plasma with platelets in the separation bag; increasing the squeezing pressure on the separation bag while preventing components from leaving the separation bag to create an over-pressure; using the over-pressure to spurt some of the platelets and plasma toward the platelet transfer bag; squeezing the separation vessel to transfer the remainder of the platelets and plasma to the platelet transfer bag to provide plasma rich platelets; squeezing the separation bag to transfer monocytes to a monocyte transfer bag; and transferring the red blood cell component to a red blood cell transfer bag.

A further object of the invention is to provide a method of separating a composite liquid into at least a first component and a second component comprising providing a separation vessel on a rotor; locating at least two transfer bags connected to the separation bag on the rotor; centrifuging the separation vessel containing the composite liquid so as to cause the sedimentation of at least the first and second components; squeezing the separation bag so as to transfer some of the first component to one of the transfer bags wherein the step of squeezing comprises stopping the transfer of the first component; releasing the squeezing step to release after the stopping step some of the squeezing pressure on the separation bag; opening a valve between the separation vessel and the first transfer bag to permit at least some of the first component to return to the separation vessel; and remixing at least the second component and the returned first component in the separation vessel.

The invention further contemplates apparatus such as apparatus for providing four component separation of a blood product comprising a separation set comprising a separation vessel; a first transfer bag; a first transfer tube connecting the first transfer bag to the separation vessel; a second transfer bag; a second transfer tube connecting the second transfer bag to the separation vessel; a third transfer bag; a third transfer tube connecting the third transfer bag to the separation vessel; a fourth transfer bag; a fourth transfer tube connecting the fourth transfer bag to the separation vessel; a rotor for receiving the separation set wherein the separation set is located on the rotor, the rotor comprising a first valve for receiving the first transfer tube; a second valve for receiving the second transfer tube; a third valve for receiving the third transfer tube; a motor to spin the rotor to sediment blood product in the separation vessel into first, second, and third, and fourth components; a first sensor to sense when the blood product is in the separation bag; a second sensor to sense the interface between air in the separation bag and the blood product; a third sensor to sense the interface between a relatively low density first component and a relatively medium density second component; a fourth sensor for sensing the top surface of the layer of the heaviest density fourth component; a squeezing apparatus for providing squeezing pressure to the separation bag to squeeze at least one of the separated first, second and third components from the separation bag through at least one of the transfer tubes to at least one of the transfer bags; a controller for controlling the spinning of the rotor and the squeezing apparatus and for receiving sensed information from the first, second, third and fourth sensors.

Other features and advantages of the invention will appear from the following description and accompanying drawings, which are to be considered exemplary only.

DESCRIPTION OF THE EMBODIMENTS

For the sake of clarity, the invention will be described with respect to a specific use, namely the separation of whole blood into four components, namely a plasma component, a platelet component, a mononuclear cell component, and a red blood cell component. It should be understood however that this specific use is exemplary only. It should also be understood that the principles can be used for collecting at least two components.

Figure 1:
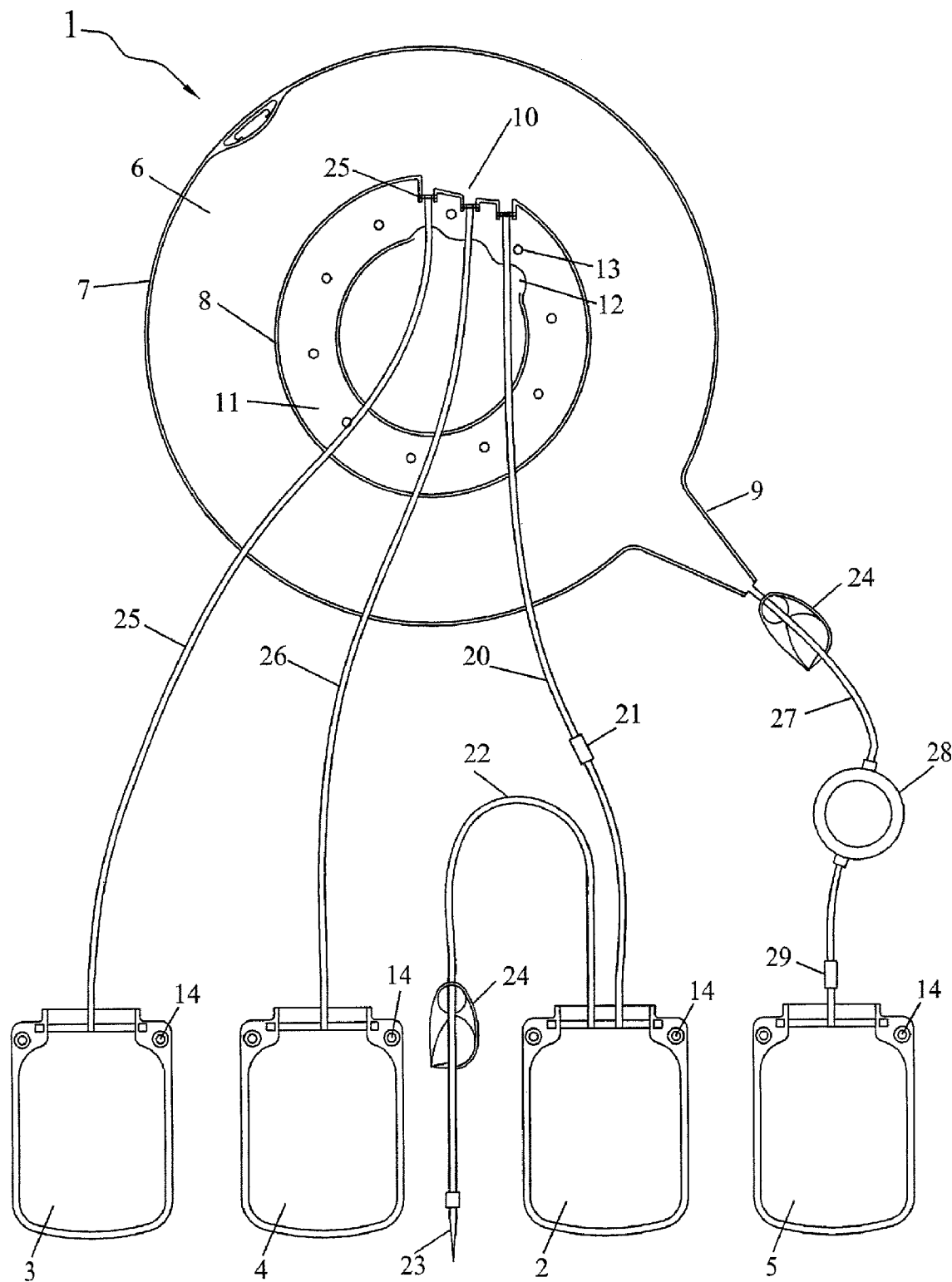
FIG. 1 is a schematic view of a set of bags designed for cooperating with a separation apparatus according to the invention.
Figure 2:
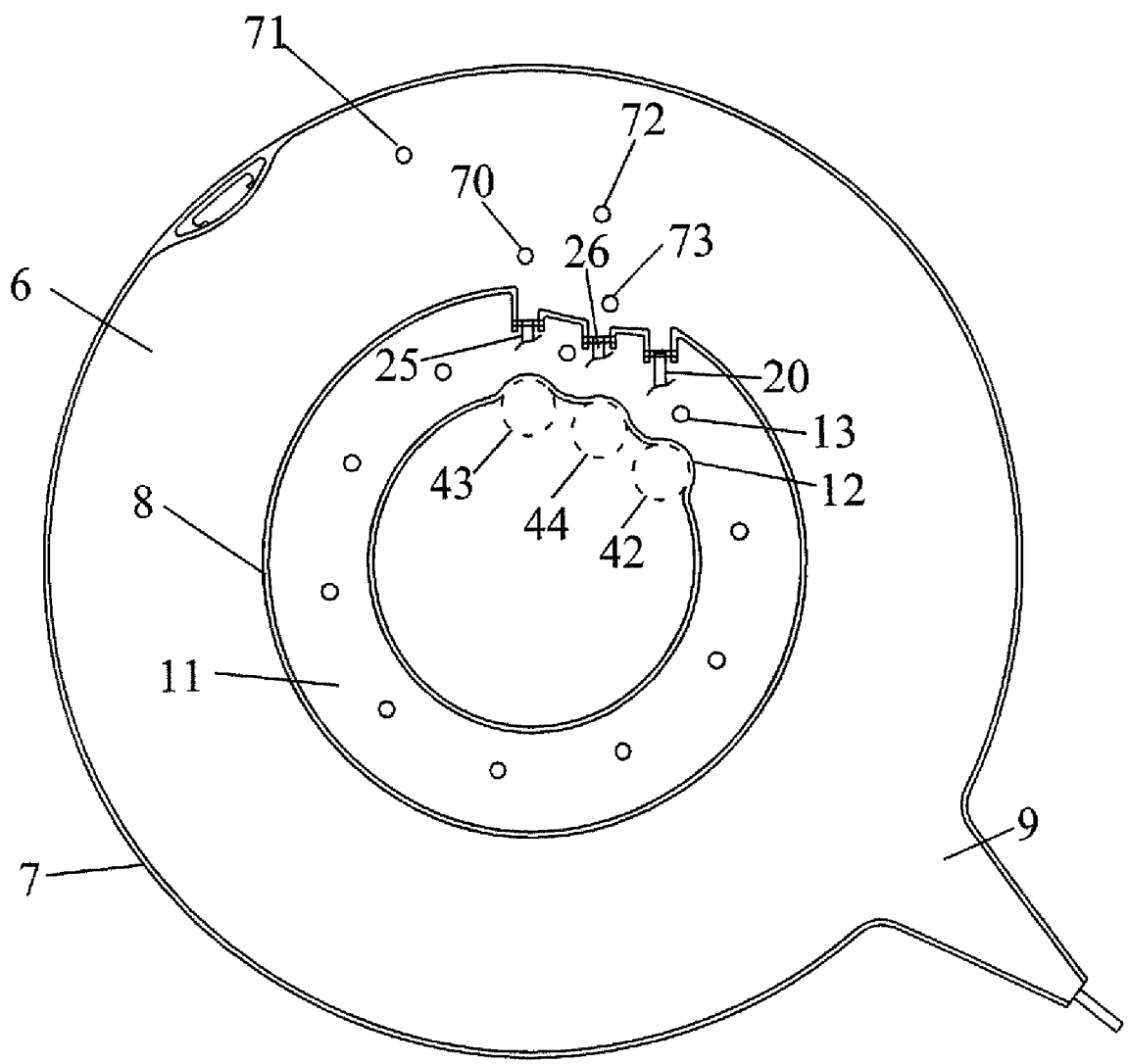
FIG. 2 is an enlarged view of the separation bag of the set of bags of FIG. 1.

FIGS. 1 and 2 show an example of a set of bags adapted to the separation of whole blood into a plasma component (essentially comprising plasma), a platelet component (essentially comprising platelets), a mononuclear cell component (comprising monocytes, lymphocytes and some red blood cells) and a red blood cell component (essentially comprising red blood cells and granulocytes). This bag set comprises a flexible separation bag 1 and four flexible satellite bags 2, 3, 4, 5 connected thereto. The separation bag 1 comprises an annular separation chamber 6 having generally circular outer and inner edges 7, 8. The outer circular edge 7 and the inner circular edge 8 of separation chamber 6 are substantially concentric. Separation chamber 6 comprises a first, acute-angled, funnel-like extension 9 protruding outwardly from its outer edge 7 for helping drain a content of the separation chamber 6 into satellite bag 5. Separation chamber 6 also comprises a second, obtuse-angled, funnel-like extension 10 protruding from inner edge 8, towards the center of bag 1, for helping funnel separated components into first, second and third satellite bags 2, 3, 4.

Separation bag 1 further comprises a semi-flexible disk-shaped connecting element 11 that is connected to inner edge 8 of annular chamber 5. Disk-shaped connecting element 11 comprises three rounded recesses 12 on its inner edge facing second funnel-like extension 10, for partially surrounding three pinch valve members of a rotor of a centrifuge to be described later (diagrammatically shown in doted line in FIG. 2). Disk-shaped connecting element 11 comprises a series of holes 13 for connecting separation bag 1 to the rotor of a centrifuge.

Satellite bag 2 has two purposes, and is successively used as a whole blood collection bag and as a mononuclear cell component bag. Satellite bag 2 is intended for initially receiving a volume of whole blood from a donor (usually about 450 ml) before the separation process, and the mononuclear cell component during the separation process. Satellite bag 2 is flat, substantially rectangular, and comprises two reinforced ears at its upper corners having holes 14 for hanging the bag. It is connected to separation bag 1 by transfer tube 20 having a first end connected to the upper edge of satellite bag 2 and a second end connected to the second funnel-like extension 10, close to inner circular edge 8. Satellite bag 2 contains a volume of anti-coagulant solution (typically about 63 ml of a solution of citrate phosphate dextrose for a blood donation of about 450 ml). A frangible connector 21 mounted on transfer tube 20 blocks a liquid flow through transfer tube 20 and prevents the anti-coagulant solution from flowing from satellite bag 2 into separation bag 1.

The bag set further comprises a collection tube 22 that is connected at one end to the upper edge of satellite bag 2 and comprises, at the other end, a needle protected by a sheath 23. Collection tube 22 is fitted with a clamp 24.

Satellite bag 3 is intended for receiving a plasma component. Satellite bag 3 is flat, substantially rectangular, and comprises two reinforced ears at its upper corners having holes 14 for hanging the bag. It is connected by a transfer tube 25 to separation bag 1. Transfer tube 25 has a first end connected to the upper edge of satellite bag 3 and a second end connected to the second funnel-like extension 10, close to inner circular edge 8, opposite the second end of the first transfer tube 20 with respect to the tip of the second funnel-like extension 10.

Satellite bag 4 is intended for receiving a platelet component. It is flat, substantially rectangular, and comprises two reinforced ears at its upper corners having holes 14 for hanging the bag. It is connected by a transfer tube 26 to the separation bag 1. Transfer tube 26 has a first end connected to the upper edge of satellite bag 4 and a second end connected to the tip of the second funnel-like extension 10.

Satellite bag 5 is intended for receiving a red blood cell component. It is flat, substantially rectangular, and comprises two reinforced ears at its upper corners having holes 14 for hanging the bag. It is connected by a transfer tube 27 to separation bag 1. Transfer tube 27 has a first end connected to the upper edge of satellite bag 5 and a second end connected to the tip of the first funnel-like extension 9. It comprises two tube segments respectively connected to the inlet and the outlet of a leuko-reduction filter 28. The tube segment connected to separation bag 1 is fitted with a clamp 24. The tube segment connected to satellite bag 5 is fitted with a frangible connector 29, which, when broken, allows a flow of liquid between separation bag 1 and satellite bag 5. The filter may be, for example, a filter of the type RC2D manufactured by Pall Corporation. Such a filter comprises a disk-shaped casing to which radial inlet and outlet ports are connected, in diametrical opposition. The casing, which is made of polycarbonate (GE Lexan HF 1140), has an internal volume of about 33 ml. It is filled with a filtering medium composed of multiple layers of a non-woven web of polyester fibers (about two micron diameter). It is understood, however, that other filters by other manufacturers can also be used. Satellite bag 5 contains a volume of storage solution for red blood cells.

Variants of the separation bag 1 may include a separation chamber 6 having an outer circular edge 7 and/or an inner circular edge 8 that are eccentric. Alternatively, a separation chamber 6 may comprise a radial wall extending from inner edge 8 to outer edge 7 so that chamber 6, instead of being annular, is C-shaped. A separation chamber 6 having any shape including an inner edge and an outer edge (the inner edge being closer to the axis of the rotor of a centrifuge than the outer edge, when the separation bag is mounted on the rotor of a centrifuge), for example the shape of a portion of annulus delimited by two lateral radial edge or a rectangular shape may also be used. In this variant, all the satellite bags may be connected to the inner edge of the separation bag.

Also, the separation bag 1 can be shaped so as to fit either on a flat support surface or on a frusto-conical support surface of the rotor of a centrifuge.

The bags and the tubes of the bag set shown in FIGS. 1 and 2 are all made of flexible plastic material appropriate to contact blood and blood components.

Figure 3:
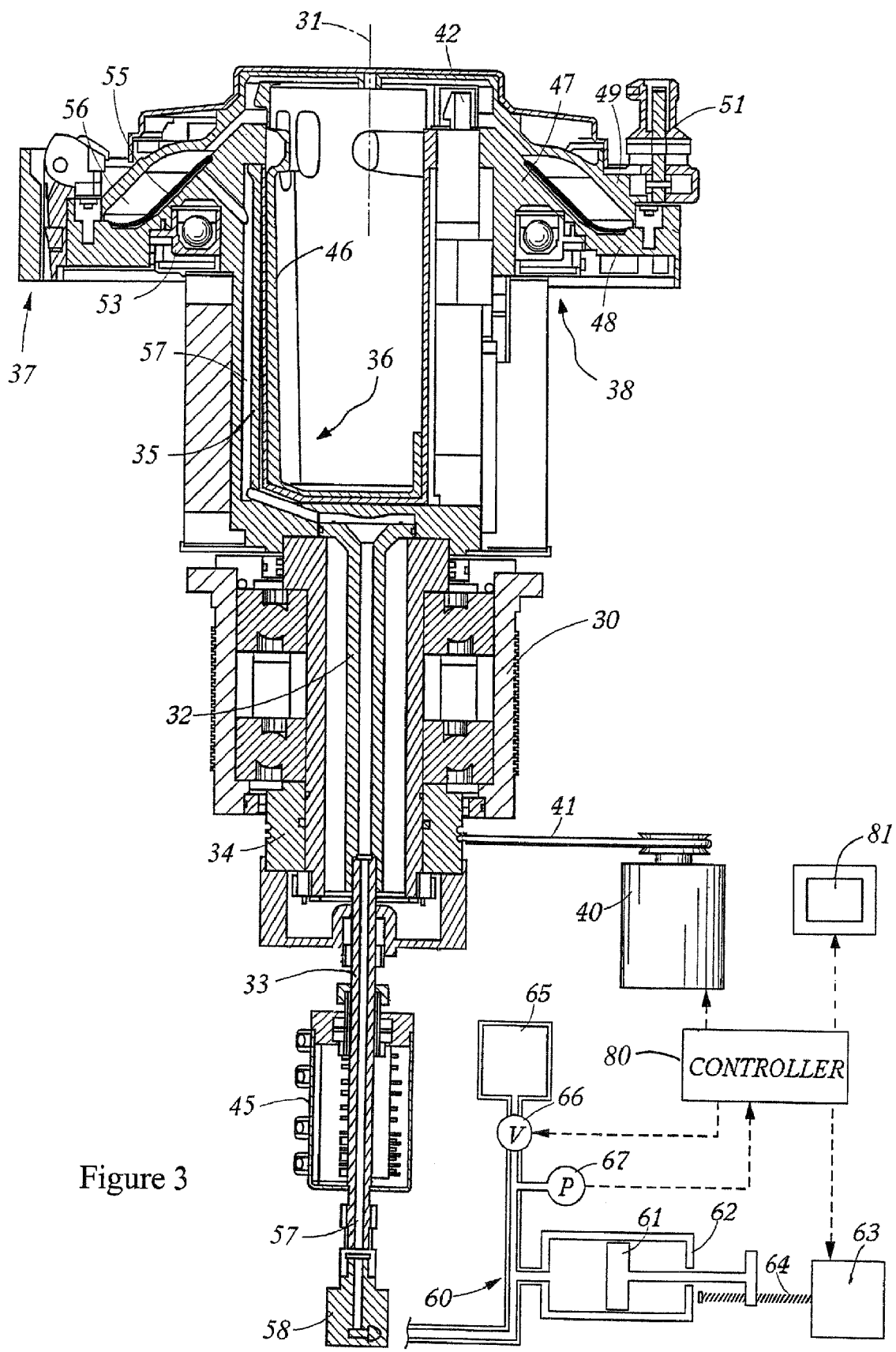
FIG. 3 is a schematic view, partly in cross-section, of a separation apparatus according to the invention.
Figure 4:
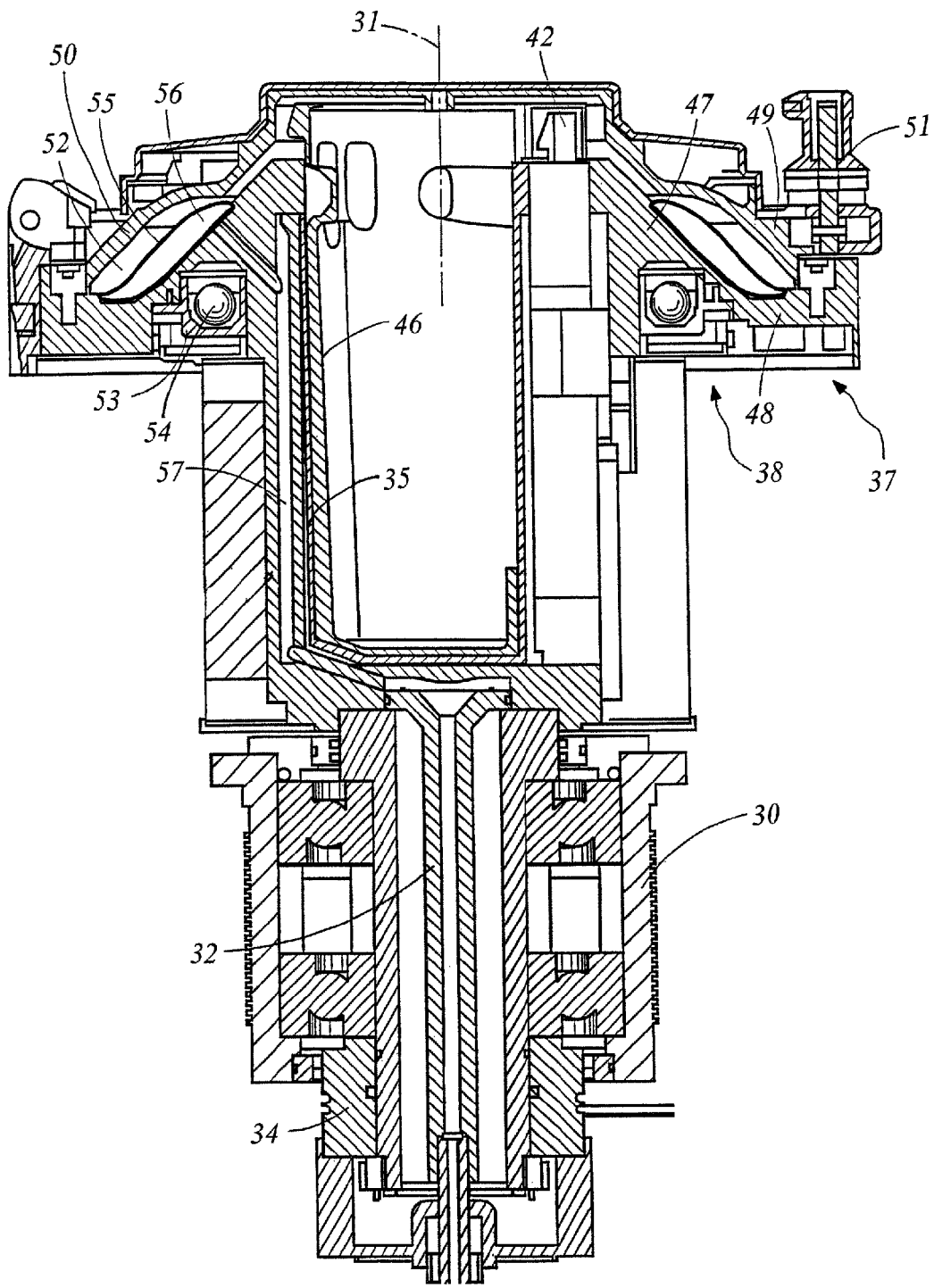
FIG. 4 is a cross-section view of the rotor of a separation apparatus according to the invention.

FIGS. 3 and 4 show an embodiment of an apparatus for separating a volume of composite liquid by centrifugation. The apparatus comprises a centrifuge adapted for receiving the set of separation bags shown in FIGS. 1 and 2, and a component transferring means for causing the transfer of separated components into the satellite bags.

The centrifuge comprises a rotor that is supported by a bearing assembly 30 allowing the rotor to rotate about a vertical central axis 31. The rotor comprises a cylindrical rotor shaft comprising a first upper portion 32 and a second lower portion 33; the upper portion 32 of the shaft extends in part through the bearing assembly 30; a pulley 34 is connected to the lower end of the upper portion 32 of the shaft; a central compartment 35 for containing satellite bags, which is connected to the rotor shaft 32, 33 at the upper end thereof; a support member 36 fitting within the central compartment 34, for supporting at least one satellite bag in a determined position within the central compartment 35; a circular turntable 37 for supporting a separation bag, which is connected to the compartment 35 at the upper end thereof, the central axes of the rotor shaft 32, 33, the compartment 35 and the turntable 37 coinciding with the rotation axis 31; and a balancing assembly 38, which is secured to the turntable 37.

The centrifuge further comprises a motor 40 coupled to the rotor by a belt 41 engaged in a groove of the pulley 34 so as to rotate the rotor about the central vertical axis 31.

The separation apparatus further comprises pinch valve members 42, 43, 44 that are mounted on the rotor for selectively blocking or allowing a flow of liquid through a flexible plastic tube, and selectively sealing and cutting a plastic tube. Each pinch valve member 42, 43, 44 comprises an elongated cylindrical body and a head having a groove that is defined by a stationary upper jaw and a lower jaw movable between an open and a closed position, the groove being dimensioned so that one of transfer tubes 20, 25, 26 of the bag sets shown in FIGS. 1 and 2 can be snuggly engaged therein when the lower jaw is in the open position. The elongated body contains a mechanism for moving the lower jaw and it is connected to a radio frequency generator that supplies the energy necessary for sealing and cutting a plastic tube. Pinch valve members 42, 43, 44 are mounted at the periphery of central compartment 35 so that their longitudinal axes are coplanar, and parallel to central axis 31 of the rotor, and their heads protrude above the rim of central compartment 35. The position of pinch valve members 42, 43, 44 with respect to separation bag 1 and transfer tubes 20, 25, 26 connected thereto when separation bag 1 is mounted on turntable 37 is shown in doted lines in FIG. 2. Electric power is supplied to pinch valve members 42, 43, 44 through a slip ring array 45 that is mounted around the lower portion 33 of the rotor shaft.

Support member 36 generally comprises a portion of wall 46 that is tilted with respect to the rotation axis 31 of the rotor. A satellite bag secured by an upper portion thereof to an upper part of the tilted wall 46 is pressed against the tilted wall 46 by centrifugation forces during rotation of the rotor and a lower portion of the satellite bag is closer to the axis of rotation than an upper portion thereof. As a result, a liquid contained in the supported satellite bag drains from the supported satellite bag into the separation bag under centrifugation forces.

Turntable 37 comprises a central frusto-conical portion 47, the upper, smaller edge of which is connected to the rim of compartment 35, an annular flat portion 48 connected to the lower, larger edge of the frusto-conical portion 47, and an outer cylindrical flange 49 extending upwards from the outer periphery of the annular portion 48. Turntable 35 further comprises a vaulted circular lid 50 that is secured to flange 49 by a hinge so as to pivot between an open and a closed position. Lid 50 is fitted with a lock 51 by which it can be blocked in the closed position. Lid 50 has an annular interior surface that is so shaped that, when lid 50 is in the closed position, it defines with the frusto-conical portion 47 and the annular flat portion 48 of the turntable 37 a frusto-conical annular compartment 52 having a radial cross-section that has substantially the shape of a parallelogram. The frusto-conical annular compartment 52 (later the "separation compartment"), which has a fixed volume, is intended for containing the separation bag 1 shown in FIGS. 1 and 2.

Balancing assembly 38, which has generally the shape of a ring, is mounted on the rotor within the space that extends between the upper end of central compartment 35 and the frusto-conical wall 47 of turntable 37. Balancing assembly 38 comprises a ring-shaped housing 53 defining a cavity whose cross-section, along a radial plane, is generally rectangular. The balancing assembly further comprises a plurality of ponderous balls 54 having a diameter that is slightly less than the radial depth of the cavity of housing 53. When the balls 54 are in contact with each other they occupy a sector of housing 52 of about 180 degrees.

The component transferring means comprises a squeezing system for squeezing the separation bag within separation compartment 52 and causing the transfer of separated components into the satellite bags. The squeezing system comprises a flexible annular diaphragm 55 that is so shaped as to line the frusto-conical portion 47 and the annular flat portion 48 of turntable 37, to which it is secured along its smaller and larger circular edges. The squeezing system further comprises a hydraulic pumping station 60 for pumping a hydraulic liquid in and out an expandable hydraulic or squeezing chamber 56 defined between flexible diaphragm 55 and turntable 37, via a duct 57 extending through the rotor from the lower end of lower portion 33 of the rotor shaft to turntable 37. Pumping station 60 comprises a piston pump having a piston 61 movable in a hydraulic cylinder 62 fluidly connected via a rotary fluid coupling 58 to rotor duct 57. Piston 61 is actuated by a stepper motor 63 that moves a lead screw 64 linked to piston rod 61. Stepper motor 63 can be controlled by discrete increments or steps, each step corresponding to a fraction of turn of the axle of motor 63, a small linear displacement of piston 61, and a small determined volume of liquid being pumped in or out of hydraulic chamber 56. Hydraulic cylinder 62 is also connected to a hydraulic liquid reservoir 65 having an access controlled by a valve 66 for selectively allowing the introduction or the withdrawal of hydraulic liquid into and from a hydraulic circuit including hydraulic cylinder 62, rotor duct 57 and the expandable hydraulic chamber 56. A pressure gauge 67 is connected to the hydraulic circuit for measuring the hydraulic pressure therein.

The separation apparatus further comprises four sensors 70, 71, 72, and 73 for detecting characteristics of the separation process occurring within a separation bag 1 when the apparatus operates. The four sensors 70, 71, 72, and 73 are embedded in lid 50 at different distances from the rotation axis 31 of the rotor, a sensor 73 being the closest to the rotation axis 31, a sensor 71 being the farthest to the rotation axis 31 and a sensor 72 and a sensor 70 occupying an intermediate position with sensor 70 being closer to the axis of rotation than sensor 72. When the lid 50 is closed, the four sensors 70, 71, 72, and 73 face separation bag 1 as shown in FIG. 2. Sensor 70 is embedded in lid 50 so as to be positioned over separation chamber 6 a short distance from the end of tube 25 connected to the second funnel-like extension 10 (plasma outlet). Sensor 70 is able to detect an interface gas/liquid, an interface between plasma and a platelet/mononuclear cell layer, an interface between platelet rich plasma and mononuclear cells, as well as red blood cells. Sensor 71 (later the "outer sensor") is embedded in lid 50 so as to be positioned over separation chamber 6 at about two third of the width of the separation chamber from the inner edge, and it is offset with respect to the second funnel-like extension 10, while being closer to the end of the second transfer tube 25 than to the respective ends of transfer tubes 20, 26. Outer sensor 71 is able to detect a liquid, e.g., blood. Sensor 72 is embedded in lid 50 so as to be positioned over separation chamber 6 at about one third of the width of the separation chamber from inner edge 8 thereof. Sensor 72 is able to detect an interface between plasma and blood cells. Sensor 73, or the inner sensor, is positioned close to transfer tube 26 (platelet outlet). This sensor is able to detect the top of the red blood cell layer. Each sensor 70, 71, 72, and 73 can comprise a photocell including an infra-red LED and a photo-detector. Electric power is supplied to the sensors 70, 71, 72 through slip ring array 45.

The separation apparatus further comprises a controller 80 including a control unit (microprocessor) and a memory for providing the microprocessor with information and programmed instructions relative to various separation protocols and to the operation of the apparatus in accordance with such separation protocols. In particular, the microprocessor is programmed for receiving information relative to the centrifugation speed(s) at which the rotor is to be rotated during the various stages of a separation process, and information relative to the various transfer flow rates at which separated components are to be transferred from the separation bag 1 into satellite bags 2, 3, 4. The information relative to the various transfer flow rates can be expressed, for example, as hydraulic liquid flow rates in the hydraulic circuit, or as rotation speeds of stepper motor 63 of hydraulic pumping station 60. The microprocessor is further programmed for receiving, directly or through the memory, information from pressure gauge 67 and from photocells 70, 71, 72, 73 and for controlling centrifuge motor 40, stepper motor 63, and pinch valve members 42, 43, 44 so as to cause the separation apparatus to operate along a selected separation protocol.

Control unit 80 is also programmed for determining and displaying on a screen 81 of the separation apparatus the actual volume of the components separated during a separation procedure, as well as the actual volume of the composite liquid (for example, whole blood) initially contained in separation bag 1.

An example of a first separation protocol aiming at the preparation of four blood components from a whole blood donation, namely a plasma component, a platelet component, a mononuclear cell component and a red blood cell component, is explained below. Alternatively, the protocol can be used for a three component collection with mononuclear cells being waste or even for at least a two component collection.

The operation of the separation apparatus along the first separation protocol is as follows:

First stage (first protocol): a bag set as shown in FIG. 1, in which satellite bag 2 contains a volume of whole blood, is set in place in the rotor of a centrifuge (as shown in FIGS. 3, 4).

At the onset of the first stage, satellite bag 2 of the bag set of FIG. 1 contains a volume of anti-coagulated whole blood (usually about 500 ml). Collection tube 22 has been sealed and cut close to satellite bag 2. Clamp 24 on transfer tube 27 connecting satellite bag 5 to separation bag 1 is closed. The four satellite bags 2, 3, 4, 5 are superposed one upon another so as to form a stack that is inserted bag loader 36 so that satellite bag 2 is adjacent the tilted wall 46 of bag loader 36. Satellite bags 2, 3, 4, 5 are secured by their upper ears to an upper part of bag loader 36, above the tilted wall 46. In this position, they are substantially located on one side of a plane containing the rotation axis 31 of the rotor, and a lower portion of satellite bag 2 containing the volume of whole blood is closer to the rotation axis 31 than an upper portion thereof.

Separation bag 1 is then laid on turntable 37 and pins (not shown) protruding on turntable 37 around the opening of central compartment 35 are engaged in holes 13 of the disk-shaped connecting element 11 of separation bag 1. Transfer tube 20 connecting satellite bag 2 to separation bag 1 is engaged in pinch valve member 42, transfer tube 25 connecting satellite bag 3 to separation bag 1 is engaged in pinch valve member 43, and transfer tube 26 connecting satellite bag 4 to separation bag 1 is engaged in pinch valve member 44. Frangible connector 21 blocking communication between satellite bag 2 and separation bag 1 is broken. Lid 49 of the rotor is closed.

Second stage (first protocol): the anti-coagulated whole blood contained in satellite bag 2 is transferred into the separation bag 1.

At the onset of the second stage, pinch valve member 42 is open and pinch valve members 43, 44 are closed. The rotor is set in motion by centrifuge motor 40 and its rotation speed increases steadily until it reaches a first centrifugation speed (e.g. about 1500 RPM) that is so selected as to be high enough to cause the transfer, under centrifugation forces, of the content of satellite bag 2 into separation bag 1, so that the whole transfer happens in a short period of time; while, at the same time, to be low enough not to cause pressure within satellite bag 2 to substantially exceed a determined pressure threshold above which hemolysis would occur; and to be low enough not to generate shearing forces in the flow of blood entering separation bag 1 that would cause hemolysis.

It has been determined that the pressure threshold above which hemolysis occurs in satellite bag 2 is about 10 PSI, and that the maximum rotation speed at which such pressure threshold is not reached and the shearing forces in the blood flow entering the separation bag do not cause hemolysis is about 1800 RPM. At a rotation speed of about 1500 RPM, it takes about one minute for transferring about 500 ml of anticoagulated blood from satellite bag 2 into separation bag 1.

When outer cell 71 detects blood, valve member 43 controlling a flow of fluid through transfer tube 25 connected to satellite bag 3 (in which a plasma component will be later transferred) is opened for a predetermined amount of time (for example, about 30 seconds) so as to allow air to vent from separation bag 1 when blood pours therein.

If outer cell 71 has not detected blood within a predetermined period of time following the start of the centrifugation process, control unit 80 causes the rotor to stop and an alarm to be emitted. This could happen in particular if frangible connector 21 has inadvertently not been broken.

Third stage (first protocol): the air present in separation bag 1 is purged into satellite bag 2, in which the mononuclear cell component is to be later transferred.

At the onset of the third stage, the whole content of satellite bag 2 has been transferred into separation bag 1, pinch valve member 42 is open, and pinch valve members 43, 44 are closed. The rotor rotates at the first rotation speed (about 1500 RPM). Pumping station 60 is actuated so as to pump hydraulic liquid at a constant flow rate (for example, about 240 ml/min) into hydraulic chamber 56 and consequently squeeze separation bag 1. The air present in separation bag 1 is expelled into satellite bag 2 for the mononuclear cell component. After a predetermined period of time following the detection of an interface air/liquid by sensor 70, the pumping station 60 is stopped and pinch valve member 42 is closed. A small residual volume of air remains in separation bag 1.

Fourth stage (first protocol): the blood within the separation chamber is sedimented to a desired level.

At the onset of this stage, pinch valve members 42 and 43 are closed. The speed of the rotor is increased steadily until it reaches a second, high, centrifugation speed (for example, about 3200 RPM, so-called "hard spin") at which the blood components will sediment at the desired level. Pinch valve member 44 is open so that any additional air can be expelled to platelet bag 4. To expel the air the pumping station is activated to pump hydraulic fluid at a constant flow rate to the hydraulic chamber to squeeze the separation bag 1. Squeezing continues until the hydraulic pressure is a predetermined variation from the constant pressure as described below.

The rotor is rotated at the second centrifugation speed for a predetermined period of time (for example, about 220 seconds), which is selected so that, whatever the hematocrit of the whole blood initially transferred in the separation chamber 1, the blood sediments therein at the end of the predetermined period to a point where the hematocrit of the outer annular red blood cell layer is about 90 and the inner annular plasma layer is substantially devoid of cells. In more detail, at the outcome of this sedimentation stage, the separation bag 1 exhibits four layers: a first inner layer mainly comprising plasma, a second intermediate layer mainly comprising platelets, a third intermediate layer mainly comprising white blood cells (lymphocytes, monocytes and granulocytes), and a fourth outer layer mainly comprising red blood cells, wherein the third and fourth layers partially overlap (the granulocytes are in part embedded in the fourth layer).

Fifth stage (first protocol): a plasma component is transferred into satellite bag 3.

At the onset of this stage, the pinch valve member 42 and 43 are closed. Pinch valve member 44 remains open. The rotor continues to rotate at the same high centrifugation speed as in the sedimentation stage. After a predetermined period of time after sensor 72 has detected the outward moving plasma/blood cell interface, which can happen before the end of the predetermined sedimentation period, pinch valve member 43 controlling access to satellite bag 3 is opened. Pumping station 60 is actuated so as to pump hydraulic liquid at a constant flow rate (for example, about 150-220 ml/min) into hydraulic chamber 56. The expanding hydraulic chamber 56 squeezes separation bag 1 and causes the transfer of plasma into satellite bag 3 and some plasma into transfer tube 26. Pinch valve 44 is closed at the turning point of increasing pressure to constant pressure as described below. Thus the majority of the plasma is transferred to bag 3. The pinch valve member 43 is closed after a predetermined period of time has elapsed following the detection of the inward moving plasma and platelet/mononuclear cell interface by the intermediate sensor 70. At the end of this stage, a first, larger, fraction of the total volume of plasma is in satellite bag 3, a second, smaller, fraction of the total volume of plasma remains in separation bag 1, and a third small fraction of the total volume of plasma has entered transfer tube 26.

The transfer flow rate of the plasma component (which is directly related to the flow rate of the hydraulic fluid or liquid) is selected to be as high as possible without disturbing the platelet layer so as to avoid contaminating the plasma component with platelets.

Control unit 80 determines the volume of plasma that has been transferred into satellite bag 3 in the following manner: first, it determines when plasma actually starts pouring into satellite bag 3; second, it counts the number of steps performed by stepper motor 63 between the time plasma actually starts pouring into satellite bag 3, and the time pumping station 60 stops pumping hydraulic liquid into hydraulic chamber 56 after sensor 70 has detected an interface between plasma and the platelet/mononuclear cells; finally, the control unit 80 calculates, from the counted number of steps and the determined small volume associated to one step, the total volume of hydraulic liquid pumped into hydraulic chamber 56 during this stage, which corresponds to the volume of plasma in satellite bag 3.

Control unit 80 determines when plasma actually starts pouring into satellite bag 3, in the following manner: it continuously records discrete successive values of the pressure of the hydraulic liquid as measured by pressure sensor 67, and it simultaneously analyses how the pressure evolves, for example by calculating, each time a new pressure value is recorded, from the average of the last four measured values, the slope of a curve representing the evolution of the pressure with respect to time, and by comparing the series of slopes so calculated; control unit 80 determines the point in time at which plasma start pouring into satellite bag 3 as corresponding to a drastic turning point between a first phase of steadily increasing pressure and a second phase of substantially constant pressure. This constant pressure as determined by pressure gauge 37 is recorded in the controller as pressure P. This turning point is also the signal for the control unit 80 to close valve 44.

Control unit 80 can be programmed to cause the actual volume of plasma in satellite bag 3, once determined, to be displayed on screen 81.

Control unit 80 also determines the volume of anti-coagulated whole blood that has been transferred into separation bag 1 during the second stage, in the following manner: it first counts the number of steps performed by stepper motor 63 between the time pumping station 60 starts pumping hydraulic fluid into hydraulic chamber 56 at the third stage (transfer of air into satellite bag 2), and the time when plasma actually starts pouring into satellite bag 3, as determined above; second, control unit 80 calculates, from the counted number of steps and the determined small volume associated to one step, the total volume of hydraulic liquid pumped into hydraulic chamber 56 until separation compartment 52 does not contain air anymore; finally, control unit 80 calculates the volume of anti-coagulated blood that is in separation chamber 1, by subtracting the volume of hydraulic liquid so calculated from a fixed volume, stored in the memory of control unit 80. This fixed volume corresponds to the fixed volume of separation compartment 52, minus the volume of diaphragm 55, minus the volume of the two superposed rings of plastic sheet delimiting separation chamber 6, and minus a fixed residual volume of hydraulic liquid in hydraulic chamber 56.

Control unit 80 can be programmed to cause the actual volume of anti-coagulated blood in separation bag 1, once determined, to be displayed on screen 81.

Sixth stage (first protocol): the platelet component is transferred into satellite bag 4.

Pinch valve member 44 controlling the access to satellite bag 4 is open and pinch valve member 42, 43 remain closed. The rotor continues to rotate at 3200 rpm. Pumping station 60 is actuated so as to pump hydraulic liquid at a first platelet flow rate into hydraulic chamber 56 and consequently squeeze separation bag 1 and cause the transfer of the platelet component and the smaller fraction of the plasma component in tube 26 into satellite bag 4. The first platelet flow rate for the platelets (for example, about 15 ml/min) is substantially lower than the flow rate (for example, about 150-220 ml/min) at which the plasma component is transferred into satellite bag 3 in the fifth stage. The first transfer flow rate of the platelet component (which is directly related to the first flow rate of the hydraulic fluid) is selected to be high enough for preventing the suspended platelets from sedimenting, without, at the same time, triggering the activation of the platelets.

After a predetermined volume of platelets has been collected as described below and after sensor 73 detects an interface between the suspended platelets and mononuclear/red blood cells, the pumping station is stopped and pinch valve member 44 is then closed.

Control unit 80 determines the volume of the platelet component that has been transferred into satellite bag 4 at this point in the procedure in the following manner: it first counts the number of steps performed by stepper motor 63 between the time pumping station 60 starts pumping hydraulic fluid into hydraulic chamber 56 following the opening of pinch valve member 44, and the time pumping station 60 is stopped after sensor 73 has detected the interface between the suspended platelets and the mononuclear/red blood cells; second, control unit 80 calculates, from the counted number of steps and the determined small volume associated to one step, the total volume of hydraulic liquid pumped into hydraulic chamber 56 during this stage, which corresponds to the volume of the platelet component transferred to satellite bag 4. This volume is stored in the control unit 80 memory.

Seventh stage (first protocol): the flow of hydraulic fluid is reversed.

After the closure of pinch valve member 44 the rotor is slowed to approximately 900 rpm. The hydraulic system is reversed to withdraw a volume Vx of hydraulic fluid from hydraulic or squeezing chamber 56 releasing some of the squeezing pressure on separation bag 1. During this reversal of hydraulic fluid separation is maintained between any platelets and the red blood cells and mononuclear layers in separation bag 1. Vx is selected by the controller based on final desired platelet volume as will be more fully explained with respect to the expression or spurt of platelets below. Vx can be indicative of the final plasma concentration in the final platelet product. Variations of Vx can be used to vary the plasma content and to provide plasma rich platelets.

Eighth stage (first protocol): plasma component returns to separation bag 1 (remixing).

The reverse pumping of hydraulic pumping station 60 is stopped, the rotor speed is increased to 3200, and pinch valve 43 is opened. This withdraws a volume of plasma Vx from satellite bag 3 corresponding to the removed volume of hydraulic fluid Vx as the transfer amount of the plasma is directly related to the transfer amount of the hydraulic fluid removed from hydraulic chamber 56. The returned plasma remixes with the platelets and red blood cells to assure any residual platelets are separated from the red blood cells. At this hard spin the red blood cells sediment out rapidly into a red blood cell layer.

Ninth stage (first protocol): the hydraulic fluid in the hydraulic chamber 56 is increased to increase the pressure on separation bag 1 with all valves closed.

All the valves 42, 43, and 44 are closed. The rotor continues to rotate at a hard spin or approximately 3200 rpm. Hydraulic pumping station 60 is activated to return hydraulic fluid to hydraulic or squeezing chamber 56. Hydraulic chamber 56 receives hydraulic fluid until the pressure exerted on separation bag 1 is pressure P plus $\Delta$P. That is, the pressure is raised higher than the constant pressure for expression to assure that the separation bag 1 is at a pressure for rapid expression or spurting as will be more fully explained below.

Tenth stage (first protocol): clearing of platelet line.

After hydraulic chamber 56 is filled with hydraulic fluid as set forth in the ninth stage above, pinch valve member 44 is opened while pinch valves 42 and 43 remain closed. The rotor continues to rotate at 3200 rpm. Some residual platelets and plasma from separation bag 1 are rapidly expressed or caused to spurt to transfer tube 26 connected to satellite bag 3 by the over pressure applied by hydraulic chamber 56. Hydraulic pumping station 60 is stationary during this rapid expression or spurt period as all the expression is the consequence of the built up pressure from the hydraulic fluid already present in hydraulic chamber 56. This spurt expression clears the transfer line 26 of any residual platelets contained therein from the platelet expression of the sixth stage.

Control unit 80 determines the volume of the spurted platelet and plasma component that is transferred into satellite bag 4 at this point in the procedure in the following manner: it first counts the number of steps performed by stepper motor 63 between the time pumping station 60 starts pumping hydraulic fluid into hydraulic chamber 56 until the pressure on the separation bag 1 is P and $\Delta$P and the pinch valve member 44 is opened. The control unit 80 calculates, from the counted number of steps and the determined small volume associated to one step, the total volume of hydraulic liquid pumped into hydraulic chamber 56 during this stage, which corresponds to the volume of the platelet with any plasma component rapidly expressed or transferred to satellite bag 4 during this stage. This volume is stored in the control unit 80 memory.

Eleventh stage (first protocol): remaining platelets are collected

Pinch valve 44 remains open. Hydraulic pumping station 60 is ramped up to provide a low flow rate of the remaining platelets/plasma or plasma rich platelets of approximately 15 ml/min until a predetermined time after the top of the red blood cell layer is detected by inner photocell 73. The predetermined time assures that the maximum number of platelets will be collected. The centrifuge or rotor continues to rotate at 3200 rpm. After the predetermined time, pinch valve 44 is closed and platelet collection is completed.

Control unit 80 determines the volume of the platelet component that has been transferred into satellite bag 4 during this stage in the following manner: it first counts the number of steps performed by stepper motor 63 between the time pumping station 60 is ramped up to start pumping hydraulic fluid into hydraulic chamber 56 and the time pumping station 60 is stopped after sensor 73 has detected the interface between the suspended platelets and the mononuclear/red blood cells; second, control unit 80 calculates, from the counted number of steps and the determined small volume associated to one step, the total volume of hydraulic liquid pumped into hydraulic chamber 56 during this stage, which corresponds to the volume of the platelet component transferred to satellite bag 4 during this stage.

To determine the total platelet volume, the control unit 80 retrieves and adds the determined volumes from the platelet collections in the sixth, tenth and eleventh stages. The control unit 80 can be programmed to display this total volume on the display screen 81.

Twelfth stage (first protocol): a mononuclear cell component is transferred into satellite bag 2.

The twelfth stage can start as soon as pinch valve member 44 is closed at the end of the eleventh stage. At the onset of this twelfth stage, the three pinch valve members 42, 43, 44 are closed. The rotor is rotated at the same centrifugation speed as previously with the flow rate being adjusted by hydraulic pumping station 60. Pinch valve member 42 controlling the access to satellite bag 2 is opened and hydraulic pumping system 60 is actuated so as to pump hydraulic liquid at a constant flow rate (for example, about 60 ml/min) into hydraulic chamber 56. The expanding hydraulic chamber 56 squeezes separation bag 1 and causes the transfer, into first satellite bag 2, of a mononuclear cell component comprising lymphocytes, monocytes, and a small amount of red blood cells. Pumping system 60 is stopped and pinch valve member 42 is closed after a predetermined volume (e.g., between 10 and 20 ml) has been transferred into satellite bag 2. The rotor continues to rotate at 3200 rpm to maintain separation between the red blood cell and mononuclear cell layers.

Control unit 80 determines the actual volume of the mononuclear cell component in satellite bag 2 by adding the volume of the mononuclear cell component actually transferred into satellite bag 2, which volume corresponds to the number of steps performed by the stepper motor between the opening and the closing of pinch valve member 42, to an empirically determined volume of whole blood remaining in satellite bag 2, which is stored in the memory of the control unit.

Control unit 80 can be programmed to cause the actual volume of the mononuclear cell component in satellite bag 2, once determined, to be displayed on screen 81.

Thirteenth stage (first protocol): the centrifugation process is ended.

The rotation speed of the rotor is decreased until the rotor stops, pumping system 60 is actuated and reversed so as to pump the hydraulic liquid from hydraulic chamber 56 at a high flow rate (for example, about 800 ml/min) until hydraulic chamber 56 is substantially empty, and pinch valve members 42, 43, 44 are actuated so as to seal and cut transfer tubes 20, 25, 26. Red blood cells remain in separation bag 1.

Fourteenth stage (first protocol): a red blood cell component is transferred into satellite bag 5.

Control unit 80 determines the volume of red blood cells remaining in separation bag 1 by subtracting, from the previously determined volume of anti-coagulated whole blood the previously determined volumes of plasma component, platelet component and mononuclear cell component.

Lid 50 of the rotor is opened and separation bag 1 connected to satellite bag 5 is removed therefrom. Clamp 24 on transfer tube 27 is opened. Frangible connector 29 blocking communication between satellite bag 5 and leuko-reduction filter 28 is broken. The storage solution contained in satellite bag 5 is allowed to flow by gravity through filter 28 and into separation bag 1 where it is mixed with the red blood cells so as to lower the viscosity thereof. The content of separation bag 1 is then allowed to flow by gravity drain through filter 28 and into satellite bag 5. The white blood cells (granulocytes and residual monocytes and lymphocytes) are trapped by filter 28, so that the ultimate packed red blood cell component in the bag 5 is substantially devoid from white blood cells.

Control unit 80 can also determine the volume of red blood cells in satellite bag 5, which will result from the actual subsequent transfer of red blood cells from separation bag 1 into satellite bag 5 at the outcome of the fourteenth stage of the first separation protocol. Control unit 80 calculates the volume of red blood cells by subtracting, from the previously determined volume of anti-coagulated whole blood, the previously determined volumes of plasma component, platelet component, mononuclear cell component, and the internal volume of leuko-reduction filter 28, and adding to the result the known volume of red blood cell storage solution contained in satellite bag 5.

Control unit 80 can be programmed to cause either one of the actual volume of the red blood cell component in separation bag 1 and the actual volume of the red blood cell component in satellite bag 5, or both, once determined, to be displayed on screen 81.

Although the over-pressure expression has been described particularly with respect to the collection of platelets it is understood that similar expression systems can be used for other blood components. Although the instant invention has been described with respect to the movement of the plasma component from the satellite bag to the separation vessel it is understood that similar principles can be used to collect other components when it is desirable to collect a component in two stages for maximum collection amount or desirable to mix components. The above protocol has been described with respect to a four component collection, namely a first component plasma, a second component platelets, a third component mononuclear cells and a fourth component red blood cells. It is understood, however, that the concepts can be used for at least a two component collection or a three component collection. It is also further understood that use of numbers, such as the designation of first and second, etc. are only for explanation purposes and the numbers do not necessarily imply any particular order.

It will be apparent to those skilled in the art that various modifications can be made to the apparatus and method described herein. Thus, it should be understood that the invention is not limited to the subject matter discussed in the specification. Rather, the present invention is intended to cover modifications and variations.

The invention claimed is:

1. A method of separating a composite liquid into at least a first component and a second component wherein the second component comprises platelets and the first component comprises plasma, comprising:

centrifuging a separation bag containing a volume of composite liquid so as to cause the sedimentation of at least the first component and the second component;

squeezing some of the first component from the separation bag to a second transfer bag;

squeezing the separation bag to transfer some of the second component, after the squeezing step to squeeze some of the first component, to a first transfer line attached to a first transfer bag and the separation bag;

stopping the transfer of the second component to the first transfer line;

squeezing the separation bag after the stopping step to build up an over-pressure in the separation bag; and transferring, using the over-pressure, a part of the second component remaining in the separation vessel to the transfer bag through the first transfer line wherein the over-pressure causes the second component to rapidly move toward the first transfer bag and to clean the first transfer line of any residual second component from the prior squeezing step to transfer the second component.

2. The method of claim 1 wherein the steps of squeezing to transfer the first and second components comprise moving an hydraulic system forward to cause hydraulic fluid to squeeze the separation bag.

3. The method of claim 2 further comprising
reversing the hydraulic system to reverse the hydraulic fluid to reduce the squeezing of the separation bag;
transferring some of the first component back from the second transfer bag to the separation vessel after the reversing step; and
remixing any first and second component in the separation bag.

4. The method of claim 3 wherein the reversing and remixing steps occur after the stopping step.

5. The method of claim 1 wherein the method is for separating the composite fluid into at least first, second, and third components wherein the centrifuging step further causes sedimentation of at least the first, second, and third components.

6. The method of claim 5 further comprising squeezing the third component into a third transfer bag connected to the separation vessel.

7. The method of claim 5 further comprising gravity-draining the third component into a third transfer bag connected to the separation vessel.

8. The method of claim 7 further comprising filtering the third component during the gravity-draining step to remove any undesired component from the third component.

9. The method of claim 1 wherein the method is for separating the composite liquid into four components wherein the centrifuging step further causes sedimentation of at least first, second, third, and fourth components.

10. The method of claim 6 wherein the third component comprises mononuclear cells.

11. The method of claim 7 wherein the third component comprises red blood cells.

12. The method of claim 9 wherein the third component comprises mononuclear cells, and the fourth component comprises red blood cells.

13. The method of claim 1 wherein the centrifuging step comprises:
rotating a centrifuge at sufficient revolutions per minute for a hard spin to cause sedimentation; and
the squeezing step to transfer some of the second component occurs at approximately the same revolutions per minute for the hard spin.

14. The method of claim 1 wherein the centrifuging step comprises:
rotating a centrifuge at sufficient revolutions per minute for a hard spin to cause sedimentation; and
the squeezing step for the first component occurs at approximately the same revolutions per minute for the hard spin.

15. The method of claim 1 further comprising sensing when the composite liquid is in the separation bag.

16. The method of claim 1 further comprising sensing the interface between the first and second components.

17. The method of claim 12 comprising sensing the interface for the red blood cells.

18. A method of adjusting the plasma concentration of a platelet product comprising
centrifuging a separation vessel containing a volume of a composite liquid into at least a plasma component and a platelet component;
squeezing the separation vessel with hydraulic fluid in a squeezing chamber to transfer some of the plasma component to a plasma transfer bag;
squeezing the separation vessel with hydraulic fluid in a squeezing chamber to transfer some of the platelets component to a platelet transfer bag;
reversing at least one of the squeezing steps by removing a volume of hydraulic fluid from the squeezing chamber;
returning a volume of the plasma component related to the volume of removed hydraulic fluid to the separation vessel;
remixing the returned volume of plasma with residual platelets in the separation vessel;
squeezing the separation vessel to transfer mixed platelets and plasma to the platelet transfer bag;
providing an over-pressure to the separation bag; and
spurting platelets to the platelet transfer bag by the force of the over-pressure prior to the squeezing step transferring mixed platelet and plasma.

19. The method of claim 18 further comprising adjusting the amount of plasma to be returned and remixed with platelets in the separation bag by adjusting the amount of hydraulic fluid to be removed.

20. The method of claim 18 wherein the providing an over-pressure step comprises squeezing the separation vessel with hydraulic fluid while preventing transfer of any components from the separation bag.

21. A method of collecting plasma, plasma rich platelets, monocytes and red blood cells from a composite blood product comprising
centrifuging a separation bag containing a volume of composite blood product so as to cause sedimentation of plasma, platelets, mononuclear and red blood cells;
squeezing the separation bag to transfer some of the plasma to a plasma transfer bag;
squeezing the separation bag to transfer some of the platelets to a platelet transfer bag;
reversing the squeezing of the separation bag to release pressure on the bag;
returning some of the plasma from the plasma transfer bag to the separation bag;
remixing some of the plasma with platelets in the separation bag;
increasing the squeezing pressure on the separation bag while preventing components from leaving the separation bag to create an over-pressure;
using the over-pressure to spurt some of the platelets and plasma toward the platelet transfer bag;
squeezing the separation vessel to transfer the remainder of the platelets and plasma to the platelet transfer bag to provide plasma rich platelets;
squeezing the separation bag to transfer monocytes to a monocyte transfer bag; and
transferring the red blood cell component to a red blood cell transfer bag.

* * * * *